United States Patent [19]
Pereira et al.

[11] Patent Number: 6,117,915
[45] Date of Patent: *Sep. 12, 2000

[54] FATTY ALCOHOL PHOSPHATE ESTER EMULSIFIER COMPOSITIONS

[75] Inventors: Abel G. Pereira, Belleville; Patrick Obukowho, Fords; Manuel Gamez Garcia, Flemington, all of N.J.; Nancy King, Avis, Pa.

[73] Assignee: Croda, Inc., Parsippany, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/999,428

[22] Filed: Dec. 29, 1997

Related U.S. Application Data

[63] Continuation-in-part of application No. 08/334,580, Nov. 4, 1994, abandoned.

[51] Int. Cl.[7] .............................. B01F 17/14; A61K 7/09; A61K 7/42
[52] U.S. Cl. .............................. 516/57; 424/59; 424/70.9; 424/70.23; 514/941
[58] Field of Search .................................... 252/312, 351, 252/DIG. 17; 424/59, 70.9, 70.23; 514/941; 516/54, 56, 57

[56] References Cited

U.S. PATENT DOCUMENTS

| | | | |
|---|---|---|---|
| 3,963,628 | 6/1976 | Park | 252/8.84 |
| 4,118,327 | 10/1978 | Seugnet | 510/521 |
| 4,140,656 | 2/1979 | Mast | 510/137 |
| 4,369,134 | 1/1983 | Deguchi et al. | 510/404 |
| 4,536,519 | 8/1985 | Suzuki et al. | 514/785 |
| 4,587,063 | 5/1986 | Kurosaki et al. | 558/146 |
| 4,670,575 | 6/1987 | Kurosaki et al. | 558/146 |
| 4,758,376 | 7/1988 | Hirota et al. | 252/DIG. 17 |
| 4,797,273 | 1/1989 | Linn et al. | 424/59 |
| 4,904,405 | 2/1990 | Kajihara et al. | 510/406 |
| 5,124,077 | 6/1992 | Kajihara et al. | 510/130 |
| 5,139,781 | 8/1992 | Birtwistle et al. | 424/70.23 |
| 5,334,387 | 8/1994 | Haugk | 510/137 |

Primary Examiner—Richard D. Lovering
Assistant Examiner—Daniel S. Metzmaier
Attorney, Agent, or Firm—Lerner, David, Littenberg, Krumholz & Mentlik, LLP

[57] ABSTRACT

An oil-in-water emulsifier composition including between about 10 percent and about 70 percent by weight of a blend of mono- and diester phosphates of alkoxylated fatty alcohols containing between about 12 and 22 carbon atoms and alkoxylated with between about 1 and about 50 moles of an alkylene oxide selected from the group consisting of ethylene oxide, propylene oxide and mixtures thereof, wherein the mono- and diester ratio is between about 10:90 and about 90:10; and between about 90 percent and about 30 percent by weight of a blend of mono- and di-ester phosphates of fatty alcohols containing between 12 and 22 carbon atoms, wherein the mono- and diester ratio is between about 10:90 and about 90:10. Emulsifying waxes, oil-in-water emulsions and microemulsions, and topical compositions formulated therefrom are also disclosed.

21 Claims, No Drawings

FATTY ALCOHOL PHOSPHATE ESTER EMULSIFIER COMPOSITIONS

CROSS-REFERENCE TO RELATED APPLICATIONS

This application is a Continuation-In-Part of U.S. patent application Ser. No. 08/334,580 filed Nov. 4, 1994, now abandoned, the disclosure of which is incorporated herein by reference.

BACKGROUND OF THE INVENTION

The present invention relates to fatty alcohol phosphate ester emulsifier compositions useful in the preparation of oil-in-water emulsions and microemulsions. The present invention further relates to emulsifying waxes, oil-in-water emulsions and oil-in-water microemulsions prepared from the fatty alcohol phosphate ester emulsifier compositions of the present invention. The emulsions and microemulsions of the present invention are particularly useful in the formulation of topical cosmetic preparations, particularly hair and skin care products in the form of lotions, creams or gels.

Mixed phosphate esters of polyalkoxylated fatty alcohols such as are disclosed in U.S. Pat. No. 3,963,628 to Park and U.S. Pat. No. 4,369,134 to Deguchi et al. have been widely used in the personal care industry as emulsifiers for oil-in-water emulsions. However, such compounds possess less than desirable emulsion stability. Phosphate mono-esters of higher fatty alcohols, such as cetyl alcohol, have also become popular as emulsifiers, but they are used only as secondary or co-emulsifiers and require the use of primary emulsifiers to achieve emulsion stability.

Phosphate ester emulsifiers for oil-in-water emulsions having improved emulsion stabilizing properties would be highly desirable.

SUMMARY OF THE INVENTION

It has now been discovered that blends of alkoxylated fatty alcohol mono- and diester phosphates with non-alkoxylated fatty alcohol mono- and diester phosphates produce oil-in-water emulsions and microemulsions possessing desirable emulsion stability. Therefore, in accordance with one embodiment of the present invention, there is provided an oil-in-water emulsifier composition consisting essentially of:

between about 10 percent and about 90 percent by weight of a blend of mono- and diester phosphates of alkoxylated fatty alcohols containing between about 12 and 22 carbon atoms and alkoxylated with between about 1 and about 50 moles of an alkylene oxide selected from the group consisting of ethylene oxide, propylene oxide and mixtures thereof, wherein the mono- and diester ratio is between about 10:90 and about 90:10; and between about 90 percent and about 10 percent by weight of a blend of mono- and diester phosphates of fatty alcohols containing between 12 and 22 carbon atoms, wherein the mono- and diester ratio is between about 10:90 and about 90:10;

provided that the total amount of alkoxylation is within a range effective to provide both emulsion stability and oil deposition on keratin-containing substrates.

The emulsifier compositions of the present invention are preferably based on fatty alcohols containing between 14 and 20 carbon atoms, and more preferably are based on a blend of 16 and 18 carbon atom fatty alcohols. The emulsifier compositions of the present invention are preferably based on a ratio of alkoxylated fatty alcohol phosphate esters and non-alkoxylated fatty alcohol phosphate esters between about 20:80 and about 80:20, and more preferably between about 30:70 and about 70:30. The ratio of mono-esters to di-esters for both the alkoxylated and non-alkoxylated fatty alcohol phosphate esters is preferably between about 20:80 and 80:20 and more preferably between about 30:70 and about 70:30.

Emulsifier compositions of the present invention are suitable for formulation in emulsifying waxes based on fatty alcohols containing from 12 to 22 carbon atoms, which serve as thickening agents for the emulsion or microemulsion and provide a convenient form in which both the fatty alcohol thickener and the emulsifier can be incorporated into the emulsion or microemulsion. Therefore, in accordance with another embodiment of the present invention, there is provided an emulsifying wax composition containing from about 5 percent to about 90 percent by weight of the emulsifier composition of the present invention blended with a fatty alcohol containing between 12 and 22 carbon atoms. The emulsifying wax compositions of the present invention are preferably based on fatty alcohols containing 14 to 20 carbon atoms, and more preferably are based on a blend of 16 and 18 carbon atom fatty alcohols. Preferred emulsifying wax compositions of the present invention contain up to about 15 percent by weight of the emulsifier compositions of the present invention.

The emulsifier compositions of the present invention, unlike fatty non-alkoxy ester phosphates, provide oil-in-water emulsions and microemulsions possessing emulsion stabilities that have long been desired by cosmetic chemists for use in personal care products. For purposes of the present invention, a stable emulsion is defined as one that does not phase-separate, as that term is understood by those of ordinary skill in the art, after storage for one month at 40° C. The oil-in-water emulsions and microemulsions prepared from the emulsifier compositions of the present invention, unlike the stable emulsions produced with fatty alkoxy ester phosphates, have the oil deposition properties of the unstable emulsions prepared using fatty non-alkoxy ester phosphates.

Oil deposition is a desirable property for emulsions and microemulsions to be used in products such as hair straighteners or relaxers. In particular, an improvement in oil deposition reduces the hair damage and irritation associated with such products. In hair relaxers and straighteners, the deposition of oil protects the hair shaft from excessive penetration of hydroxide ion into the hair shaft, which is the cause of hair damage. Oil release by the emulsion onto the hair shaft acts as a protective barrier. Afro-American hair that has been straightened or relaxed with emulsions or microemulsions prepared from the emulsifier compositions of the present invention shows significantly less cuticle damage compared to hair straightening or relaxing emulsions and microemulsions based on other emulsifiers. This reduction in cuticle damage is the result of the controlled oil release and deposition from the emulsion.

The oil deposition properties of the emulsifier compositions of the present invention are also useful in the preparation of other topical emulsion and microemulsion products for keratin-containing substrates, such as sunscreens, wherein the emulsier compositions of the present invention enhance the Sun Protection Factor (SPF) of the sunscreens while greatly improving substantivity, i.e., "wash off" resistance.

Therefore, in accordance with further embodiments of the present invention, there is provided an oil-in-water emulsion containing from about 2 to about 80 percent by weight of an oil phase, from about 10 to about 98 percent by weight of a water phase and the emulsifier composition of the present invention in an amount between about 10 and about 40 percent by weight relative to the oil phase. There is also provided an oil-in-water microemulsion containing from about 5 to about 80 percent by weight of an oil phase, from about 20 to about 95 percent by weight of a water phase and the emulsifier composition of the present invention in an amount between about 100 percent and about 300 percent by weight relative to the oil phase.

The emulsions and microemulsions of the present invention enable cosmetic formulation chemists to produce products with a combination of emulsion stability and oil release heretofore unknown in the art.

DETAILED DESCRIPTION OF THE PREFERRED EMBODIMENT

The oil-in-water emulsifier compositions of the present invention are a blend of mono- and diester phosphates of alkoxylated and non-alkoxylated fatty alcohols containing between 12 and 22 carbon atoms. Preferred fatty alcohols contain between 14 and 20 carbon atoms. Most preferably, a fatty alcohol blend known as cetearyl alcohol is employed, which is a blend of cetyl and stearyl alcohols, which contain 16 and 18 carbon atoms, respectively.

The phosphate esters of the alkoxylated and non-alkoxylated fatty alcohols of the present invention are formed by reacting alkoxylated and non-alkoxylated fatty alcohols, respectively, with phosphorous pentoxide ($P_2O_5$). The alkoxylated fatty alcohols preferably have between about 2 and about 20 moles of the alkoxylating moieties present for each fatty alcohol moiety and are preferably either polyethoxylated, polypropoxylated or both polyethoxylated and polypropoxylated. Therefore, preferred alkoxylated fatty alcohols for use in accordance with the present invention have the structural formula of Formula I:

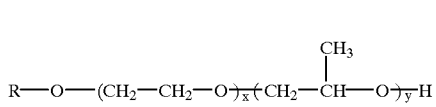

(I)

wherein R is a saturated or unsaturated, substituted or unsubstituted fatty moiety containing from 12 to 22 carbon atoms. X and Y are independently zero or integers from 1 to 50, inclusive, and the sum of X and Y is between 1 and 50, inclusive.

The non-alkoxylated fatty alcohols suitable for use in accordance with the present invention have the structural formula of Formula II:

R—OH  (II)

R is the same as described above with respect to Formula I. As is well understood by those of ordinary skill in the art, fatty alcohols are derived from fatty acids, and for this reason, groups such as R are defined as fatty moieties. Fatty alcohols are often commercially prepared from a mixture of fatty acids and contain a mixture of fatty moieties. Therefore, in accordance with the present invention, R may represent a blend of fatty moieties.

Saturated, unsubstituted fatty moieties containing from 14 to 20 carbon atoms are preferred, and, as noted above, a 16 and 18 carbon atom fatty moiety blend, known as a cetearyl blend, is most preferred.

The alkoxylated fatty alcohol depicted in Formula I is prepared by the alkoxylation of the fatty alcohol of Formula II. In the above-depicted alkoxylated fatty alcohol of Formula I, X and Y are preferably independently selected from integers from 2 to 20, inclusive, with the sum of X and Y preferably being between 2 and 20, inclusive.

The alkoxylated fatty alcohols of Formula I are prepared by initially reacting, either sequentially, or in their mixed forms, the fatty alcohols of Formula II with an epoxide, preferably ethylene oxide, propylene oxide, or mixtures thereof, in the presence of an acidic or basic catalyst. It is typical of propylene oxide to branch upon opening of the epoxide ring. Catalysts suitable for this reaction are well-known in the art and include, for example, organic and inorganic alkalies such as alkali metal oxides and hydroxides, e.g., potassium hydroxide, sodium methoxide, sodium borohydride, protic and Lewis acids, e.g., boron trifluoride, stannic chloride and sulfuric acid. Amines, quaternary ammonium compounds, water and other acids may also be employed. Mixtures of catalysts may also be employed. Certain reactive substrates known in the art, for example, acetylenic alkanols, may eliminate the need for such catalysts.

Preferably, a basic catalyst is used in this reaction and most preferably from about 0.1 to about 2.0 weight percent of potassium or sodium hydroxide, sodium methoxide, sodium borohydride or mixtures thereof, based on the weight of the fatty alcohol. The reaction is carried out under anhydrous conditions to avoid formation of by-products, and at a temperature which is preferably in the range of from about 110° C. to about 200° C., although higher temperatures may be utilized.

The reaction can be carried out at substantially atmospheric pressure, although it is preferably carried out in an autoclave at pressures of from about 10 psig to about 80 psig. The amount of ethylene oxide or propylene oxide introduced to the reaction zone, and the duration of reaction time, determines the numbers of moles of such components added to the fatty alcohol of Formula II, as is well known by those of ordinary skill in the art. In Formula I, X represents the number of moles of ethylene oxide which are incorporated into each alkoxylated fatty alcohol chain. Likewise, Y represents the number of moles of propylene oxide that are incorporated into the alkoxylated fatty alcohol chain. As will be readily appreciated by those of ordinary skill in the art, stoichiometric quantities of fatty alcohols, ethylene oxide and propylene oxide are reacted together, and stoichiometric quantities of the alkoxylated fatty alcohol and $P_2O_5$ are then reacted together to form the mono- and di-phosphate ester alkoxylated fatty alcohol blend.

For alkoxylation reactions in which the fatty alcohol is both ethoxylated and propoxylated, that is, when neither X nor Y is zero, the alkoxylation reaction is preferably carried out sequentially in that the fatty alcohol is first reacted with the propylene oxide and after complete reaction, the ethylene oxide is introduced into the reaction. After complete reaction of the ethylene oxide, an acid, e.g., phosphoric acid or acetic acid, is introduced into the reaction mixture to neutralize the basic catalyst.

The oil-in-water emulsifier compositions of the present invention, in addition to being a blend of alkoxylated and non-alkoxylated fatty alcohol phosphate esters, are also mono- and diester phosphate blends of both the alkoxylated and non-alkoxylated fatty alcohol phosphate esters. Thus, the alkoxylated fatty alcohol of Formula I, prepared as described above, is next reacted in a conventional phosphating reaction with $P_2O_5$ to form a mono- and diester phosphate alkoxylated fatty alcohol blend.

The phosphating reaction is typically performed by combining stoichiometric quantities of the alkoxylated fatty alcohol and the $P_2O_5$. As is well understood by those of ordinary skill in the art, the ratio of the two reagents will depend upon the ratio of mono- and diester phosphates desired. To obtain significant quantities of diester in the first place, a stoichiometric excess of $P_2O_5$ should be employed, with greater excess levels of $P_2O_5$ employed to increase the level of diester obtained. A 1:3 molar ratio of $P_2O_5$ to alkoxylated fatty alcohol is preferred.

The alkoxylated fatty alcohol is heated to a temperature between about 35° C. and about 90° C., and preferably at a temperature between about 50° C. and about 80° C., and then combined with mixing with $P_2O_5$ to form a reaction mixture. The alkoxylated fatty alcohol is a liquid at this temperature, therefore, a reaction solvent is not needed. The reaction is then allowed to continue until essentially complete, typically until about 10 percent or less of unreacted alkoxylated fatty alcohol and trace amounts of unreacted $P_2O_5$, now in the form of phosphoric acid, remain, usually about four hours. The reaction mixture is then recovered as a mono- and diester phosphate blend of alkoxylated fatty alcohols.

The alkoxylated fatty alcohol phosphate ester blend is then combined with a mono- and diester phosphate blend of non-alkoxylated fatty alcohols. The phosphate ester blend of non-alkoxylated fatty alcohols is prepared essentially the same as the phosphate ester blend of the alkoxylated fatty alcohols, by reacting stoichiometric quantities of the fatty alcohol of Formula II and $P_2O_5$ essentially in the same manner as described above for the alkoxylated fatty alcohol phosphate ester blend.

As noted above, mixed forms of fatty alcohols containing from 12 to 22 carbon atoms can be employed. Therefore, the resulting phosphate ester blends of alkoxylated and non-alkoxylated fatty alcohols can contain mixtures of alkoxylated and non-alkoxylated fatty alcohol phosphate esters containing from 12 to 22 carbon atoms.

The oil-in-water emulsifier compositions of the present invention are then prepared by blending the mono- and di-phosphate ester blends of alkoxylated fatty alcohols with the mono- and diester phosphate blends of non-alkoxylated fatty alcohols. Quantities of the alkoxylated and non-alkoxylated phosphate esters are added to a stirred vessel and heated with mixing at a temperature between about 60° C. and about 90° C., and preferably at a temperature between 75° C. and 85° C., until a uniform homogeneous mixture is obtained, typically about 30 minutes.

The amount of alkoxylated fatty alcohol phosphate esters blended with non-alkoxylated fatty alcohol phosphate esters will depend upon the ultimate ratio of phosphate esters of alkoxylated and non-alkoxylated fatty alcohols desired. The emulsifier compositions of the present invention contain between about 10 percent and about 90 percent of alkoxylated fatty alcohol phosphate esters and between about 90 percent and about 10 percent of non-alkoxylated fatty alcohol phosphate esters. Preferred emulsifier compositions contain the ratio of alkoxylated fatty alcohol phosphate esters to non-alkoxylated fatty alcohol phosphate esters between about 20:80 and about 80:20, and more preferably between about 30:70 and about 70:30. The desired ratio is obtained by combining the alkoxylated fatty alcohol phosphate esters and non-alkoxylated fatty alcohol phosphate esters on a weight ratio basis.

The total amount of alkoxylated fatty alcohol ester groups should not be so great that the emulsifier behaves equivalently to emulsifiers containing 100 percent alkoxylated fatty alcohol esters, i.e., there would be good emulsion stability but ineffective oil deposition. That is, the total amount of alkoxylation should be within a range effective to provide both emulsion stablity and oil deposition on keratin-containing substrates. For example, when the ratio of monoester phosphate to diester phosphate is less than 50:50, the emulsifier compositions of the present invention preferably contain at least 30 percent by weight of non-alkoxylated fatty alcohol phosphate esters.

The completed reaction mixture is recovered as the oil-in-water emulsifier composition of the present invention. As noted above, the emulsifier compositions of the present invention may advantageously be formed into a flaked product, which is obtained by conventional flaking processes, such as by feeding the emulsifier composition in the molten state to a stainless steel conveyor belt wherein it is cooled to form a solid film that is scraped from the conveyor belt with a blade. The unique consistency of the emulsifier compositions of the present invention cause the compositions to flake upon scraping, which flakes do not subsequently "block" or re-solidify upon bulk storage.

The emulsifier compositions of the present invention may be formulated as emulsifying waxes. Emulsifying waxes are essentially a blend of the emulsifier compositions of the present invention with a fatty alcohol containing from 12 to 22 carbon atoms. Oil-in-water emulsions typically contain fatty alcohol thickening agents, and fatty alcohol based emulsifying waxes represent a convenient form by which fatty alcohols may be added to oil-in-water emulsions in combination with an appropriate quantity of emulsifier. Thus, the amount of the emulsifier composition of the present invention combined with a fatty alcohol to form an emulsifying wax will depend upon the ratio of fatty alcohol to emulsifier in the oil-in-water emulsion to be prepared. Therefore, emulsifying waxes in accordance with the present invention may contain from about 5 percent to about 90 percent by weight of the emulsifier composition of the present invention, although preferred emulsifying waxes will contain up to about 15 percent by weight of the emulsifier composition of the present invention.

Preferred emulsifying waxes in accordance with the present invention will be based upon one or more fatty alcohols containing from 14 to 20 carbon atoms. The cetearyl alcohol blend of 16 and 18 carbon atom fatty alcohols is most preferred.

Like the oil-in-water emulsifier compositions of the present invention, the emulsifying waxes of the present invention may advantageously be prepared in flake form. The emulsifying waxes of the present invention may be flaked by the same procedure described above with respect to the emulsifier compositions of the present invention.

The emulsifier compositions of the present invention are primarily useful as emulsifiers in the preparation of oil-in-water emulsions and microemulsions. Oil-in-water emulsions in accordance with the present invention combine an oil phase, a water phase and an amount of the emulsifier composition of the present invention effective to form an emulsion of the oil and water phase. Likewise, oil-in-water microemulsions in accordance with the present invention combine an oil phase, a water phase and an amount of the emulsifier composition of the present invention effective to form a microemulsion of the oil and water phases.

Typical emulsions contain an oil phase at a level between about 2 and about 80 percent by weight, preferably between about 5 and about 60 percent by weight, and more preferably between about 15 and about 40 percent by weight; and a water phase at a level between about 10 percent and about 98 percent by weight, preferably between about 20 and about 80 percent by weight, and more preferably between about 40 percent and about 70 percent by weight, based on the total emulsion weight. The emulsifier composition is then present in an amount between about 10 percent and about 40 percent by weight, and preferably between about 15 percent and about 30 percent by weight, based upon the weight of the oil phase. The level of emulsifier at about 20 percent by weight of the oil phase is most preferred.

For microemulsions, significantly higher levels of emulsifier are used, so that the oil droplets formed are so small that the emulsion is transparent. Typically, the emulsifier is present at a level greater than or equal to that of the oil phase up to a level of about 300 percent by weight of the oil phase. A level of between about 150 and about 275 percent by weight of the oil phase is preferred, with a level of between about 225 percent and about 250 percent of the oil phase being more preferred. Such microemulsions typically contain an oil phase at a level of between about 5 percent and about 80 percent by weight, and preferably between about 20 percent and about 40 percent by weight. The water phase is typically at a level between about 20 percent and about 95 percent by weight, preferably between about 30 and about 70 percent by weight, and most preferably between about 40 percent and about 60 percent based on the total weight of the microemulsion.

The oil-in-water emulsions of the present invention are formulated utilizing techniques that are well-known in the art. Typically, all water-soluble ingredients are mixed together to form the water phase and all water-insoluble ingredients are mixed together to form the oil phase. The two phases are then combined with the emulsifier composition of the present invention and mixed until an emulsion is formed.

The microemulsion compositions of the present invention are formulated in a similar manner, particularly as described in copending and commonly-owned U.S. patent application Ser. No. 08/052,557, filed Apr. 23, 1993, now abandoned, the disclosure of which is incorporated herein by reference. The emulsifier compositions of the present invention are substituted for the surface active agents described in that application.

The emulsions and microemulsions of the present invention are particularly useful in the formulation of topical cosmetic preparations, particularly hair and skin care products in the form of lotions, creams or gels. The emulsions and microemulsions are useful in the formulation of cold creams, anti-perspirants, hand, skin, hair and nail lotions, skin moisturizers, shaving preparations, topical pharmaceutical ointments, lipsticks, lip gloss, lip balms and the like, cleansing creams, eye makeup formulations, sun screens, cosmetic emulsions or gels in general, hair dressing preparations and hair care products such as cream rinses, shampoos, conditioners, hair coloring products, neutralizing agents for permanent waving solutions and hair relaxers, and the like, liquid hand and body soaps, and bath additives such as bath gels or foaming baths, and the like.

The emulsions and microemulsions of the present invention unexpectedly provide unique properties to permanent waving, hair relaxer and depilatory formulations. Hair relaxer formulations are used to straighten naturally or artificially curly hair. Permanent waving products, hair relaxers and depilatories may be prepared as emulsions that are formulated to a high pH (typically between pH 11–13.5) with protein hydrolyzing or reducing agents.

Suitable protein hydrolyzing or reducing agents, and the amounts to be employed in permanent waving, hair relaxer and depilatory products are described in the above-referenced U.S. patent application Ser. No. 08/052,557 now abandoned. The protein hydrolyzing agents disclosed include alkaline earth metal hydroxides and alkali metal hydroxides, ammonium hydroxide, ethanolamine and other basic amines. The protein reducing agents disclosed include metal or ammonium thioglycolates, metal or ammonium sulfites, metal or ammonium bisulfates, cystine and its salts. In general, the protein hydrolyzing or reducing agents can be used at levels between about 0.5 percent and about 18 percent by weight based on the total composition. The amount of such agents used in hair relaxers is generally considerably less than the amount used in dipilatories, and protein hydrolyzing agents are generally not used in permanent waving products.

Permanent waving products and hair relaxer products prepared with the emulsions and microemulsions of the present invention possess an unexpectedly thixotropic rheology in that the emulsion decreases in viscosity when shear is applied. This makes the permanent waving or hair relaxer preparation easier to apply to one's hair and also allows the product to spread onto the hair shaft more evenly, thereby allowing more consistent results to be achieved.

Accordingly, suitable active agents for use in topical preparations prepared from emulsions and microemulsions of the present invention include UV-absorbing agents, aqueous moisturizing agents, oily moisturizing agents, film-forming polymers, thickening agents, secondary emulsifiers other than said mono- and diester phosphates of said alkoxylated and non-alkoxylated fatty alcohols, antiseptic agents, skin conditioning agents, hair conditioning agents, deodorant actives, humectants, rheological modifiers, the above-mentioned protein reducing agents or protein hydrolyzing agents for permanent wave and hair relaxer products, and the like. The secondary emulsifier may be a detergent surfactant, which may include a variety of surfactants of the anionic type, non-ionic type, amphoteric type, and mixtures thereof. The skin conditioning agents and hair conditioning agents include emollients.

The emulsion and microemulsion based topical preparations are formulated utilizing techniques that are well-known in the art. Typically, the water-soluble ingredients are dissolved in the water-phase and the water-insoluble ingredients are combined with the oil phase prior to formation of the emulsion. Typically, the ingredients are combined with mixing and the addition of heat if necessary until uniform, homogeneous phases are formed. The two phases are then combined with the addition of the emulsifier composition of the present invention to form an emulsion or microemulsion based topical preparation.

Those of ordinary skill in the art can readily identify whether a particular active agent is water-soluble or water-insoluble and therefore whether it should be included in the water phase or oil phase of the emulsion. Likewise, whether the topical preparation will be based on an emulsion or microemulsion is more or less an aesthetic determination based upon whether a milky, opaque product is desired, or whether a clear gel-like microemulsion is preferred. In selecting the microemulsion product form, potential skin irritation from the use of elevated levels of emulsifier should be considered.

The topical preparations of the present invention therefore include one or more of the above-listed active agents. Such ingredients may be present at a level from about 0.5 percent to about 30 percent w/w, and preferably from about 5 percent to about 20 percent w/w.

As noted above, surfactants of the anionic type, non-ionic type, amphoteric type and mixtures thereof may be utilized as active agents. Suitable anionic detergents include sodium lauryl sulfate, sodium oleyl succinate, ammonium lauryl sulfosuccinate, sodium lauryl ether sulfate, ammonium lauryl sulfate, sodium dodecylbenzene sulfonate, triethanolamine dodecylbenzene sulfonate, sodium N-lauroyl sarcosinate, sodium laureth sulfate, triethanolamine lauryl sulfate, and the like.

Suitable amphoteric or ampholytic detergents include N-lauryl-N'-carboxymethyl-N-(2-hydroxyethyl)ethylenediamine, cocobetaine, the Miranol compounds in U.S. Pat. Nos. 2,528,378 and 2,781,354, cocoamidopropyl hydroxysultaine, lauroampho diacetate, cocoamidopropylbetaine, and the like. Other suitable amphoteric detergents include the quaternary cycloimidates, betaines and sultaines disclosed in U.S. Pat. No. 3,964,500. Non-ionic surfactants include polysorbate 20, laurylamide DEA, sucrose monococoate and the like. Cationic detergents such as behenalkonium chloride, quaternium-26, cetrimonium chloride, and the like, may also be used.

Among the preferred emollients that may be used with the topical preparations of the present invention are the polyalkoxylate fatty alcohol diesters and triesters of aliphatic and aromatic dicarboxylic and tricarboxylic acids disclosed by U.S. Pat. No. 5,302,377, the disclosure of which is incorporated herein by reference. Particularly preferred are the polyalkoxylated fatty alcohol triesters of citric acid available from Croda, Inc., of Parsippany, N.J.

Among the preferred UV-absorbing agents that may be used with the topical preparations of the present invention are the substantive water-soluble cationic UV-absorbing compounds disclosed by U.S. patent application Ser. No. 08/283,575 filed Aug. 1, 1994, now U.S. Pat. No. 5,601,811, the disclosure of which is incorporated herein by reference. Particularly preferred products are also available from Croda, Inc., of Parsippany, N.J.

The topical preparations of the present invention, in addition to including one or more active ingredients in an oil-in-water emulsion or microemulsion may also include coloring agents, fragrances, proteins, salts, preservatives, essential oils, and the like. These additional components may be added in various amounts as is well-known in the cosmetic formulation art. Such ingredients need not be added prior to the emulsion formation, but may instead be combined with the emulsion with mixing and the addition of heat if necessary until a uniform, homogeneous product is formed.

The following non-limiting examples set forth hereinbelow illustrate certain aspects of the present invention. They are not to be considered limiting as to the scope and nature of the present invention.

EXAMPLES

Example 1

Preparation of Lauryl Phosphate

A 2,000 mL four-necked round-bottom flask was charged with 131.6 g (3.0 moles) of lauryl alcohol. The material was heated to 65° C. and 236 g (1.0 mole) of phosphorous pentoxide ($P_2O_5$) was added with stirring. The mixture was allowed to react for four hours. The final product was cooled and recovered as lauryl phosphate having an acid value of 234 mg KOH, a diester content of 50.1 percent and a monoester content of 39.8 percent.

Example 2

Preparation of PEG-5 Behenyl Phosphate

Ethylene oxide was bubbled into 596.8 g of behenyl alcohol in the presence of potassium hydroxide catalyst until five moles of ethylene oxide were added per mole of behenyl alcohol, thus obtaining an off-white solid (PEG-5 behenyl alcohol ether) as the major product.

A four-necked flask was charged with 920.26 g (3.0 moles) of the PEG-5 behenyl ether and the material was heated to 65° C., followed by the addition of 78.9 g of $P_2O_5$, with stirring. The reaction mixture was allowed to stir for four hours. The final product was recovered as PEG-5 behenyl phosphate having an acid value of 126.5 mg KOH, a diester content of 61 percent and a monoester content of 37.4 percent.

Example 3

Preparation of PEG-5 Behenyl Phosphate-Lauryl Phosphate Emulsifier Composition To a stirred vessel was added 60 percent w/w of the PEG-5 behenyl phosphate of Example 2 and 40 percent w/w of the lauryl phosphate of Example 1. The vessel contents were heated to 70° C. and allowed to mix for 30 minutes, and then recovered as a mixture of mono- and diester phosphates of PEG-5 behenyl alcohol and lauryl alcohol having an acid value of 169.5 mg KOH.

Examples 4–18

Emulsifier compositions in accordance with the present invention were prepared over a wide range of monoester to diester ratios, as well as a wide range of ratios of non-alkoxylated fatty alcohol phosphate esters to alkoxylated fatty alcohol phosphate esters. The samples were identified as set forth in Table I:

TABLE I

| Ester Distribution (%) | | Fatty Alcohol Ratio | | Emulsifier |
|---|---|---|---|---|
| Mono Ester | Di Ester | % Non-Alkoxy | % Alkoxy | Sample ID |
| 90 | 10 | 90 | 10 | A |
| 90 | 10 | 50 | 50 | B |
| 90 | 10 | 10 | 90 | C |
| 50 | 50 | 90 | 10 | D |
| 50 | 50 | 50 | 50 | E |
| 50 | 50 | 10 | 90 | F |
| 10 | 90 | 90 | 10 | G |
| 10 | 90 | 50 | 50 | H |
| 10 | 90 | 10 | 90 | I |
| 90 | 10 | 100 | 0 | J |
| 50 | 50 | 100 | 0 | K |
| 10 | 90 | 100 | 0 | L |
| 90 | 10 | 0 | 100 | M |
| 50 | 50 | 0 | 100 | N |
| 10 | 90 | 0 | 100 | O |

The alkoxylated alcohol samples were prepared using PEG-10 Cetearyl Alcohol while Cetearyl alcohol was used as the non-alkoxy alcohol. The pure mono and diester phosphates were produced using the teachings of Kurosaki et al., U.S. Pat. Nos. 4,670,575 and 4,587,063, respectively. Batches of PEG-10 Cetearyl Alcohol—mono ester, Cetearyl Alcohol—mono ester, PEG-10 Cetearyl Alcohol—diester, and Cetearyl Alcohol—diester were produced. These products were then used to prepare the 15 blends, labeled A through O, shown in Table I.

Formulation Evaluation

The 15 blends were used to prepare emulsions at three emulsifier concentrations, 5.75%, 25% and 48.6%. The objective was to test the emulsifier at levels less than 10%, about 25% and greater than 40%.

The emulsifier levels were determined based on the oil phase the emulsion as is common practice to those familiar with the art. The emulsion formulas BW-AP1, BW-AP2 and BW-AP3 were prepared as set forth in Table II.

TABLE II

| INGREDIENT | BW-AP1(%) | BW-AP2(%) | BW-AP3(%) |
|---|---|---|---|
| Petrolatum | 21.00 | 13.00 | 15.00 |
| Mineral Oil | 15.00 | 10.00 | 10.00 |
| Emulsifier | 2.50 | 8.25 | 17.00 |
| CRODACOL 1618 | 7.50 | 10.00 | 10.00 |
| Deionized Water | 44.85 | 49.45 | 38.36 |
| Propylene Glycol | 3.00 | 3.00 | 3.00 |
| Sodium Hydroxide | 2.15 | 2.30 | 2.64 |
| Deionized Water | 4.00 | 4.00 | 4.00 |

Formula BW-AP1 was used in the <10% emulsifier study, BW-AP2 was used in the 25% emulsifier study and BW-AP3 was used in the >40% emulsifier study. A total of 45 emulsions were prepared, the stability observations for which are set forth in Table III. CRODACOL 1618 is a mixture of cetyl and stearyl alcohols, also known as cetearyl alcohol

TABLE II

| Sample ID | Emulsion BW-AP1 | Emulsion BW-AP2 | Emulsion BW-AP3 |
|---|---|---|---|
| A | stable | stable | stable |
| B | stable | stable | stable |
| C | stable | stable | stable |
| D | stable | stable | stable |
| E | stable | stable | stable |
| F | stable | stable | stable |
| G | stable | stable | stable |
| H | stable | stable | stable |
| I | stable | stable | stable |
| J | unstable | unstable | unstable |
| K | unstable | unstable | unstable |
| L | unstable | unstable | unstable |
| M | stable | stable | stable |
| N | stable | stable | stable |
| O | stable | stable | stable |

The emulsion stability was tested in a 40° C. oven for one month. It was noted that blends J, K and L, which were made from 100% non-alkoxylated alcohol ester phosphate, produced unstable emulsions. Blends M, N and O, which were made from 100% alkoxylated alcohol, were stable.

The samples chosen for oil deposition studies are set forth in Table IV:

TABLE IV

| Ester Distribution (%) | | Fatty Alcohol Ratio | | Emulsifier |
|---|---|---|---|---|
| Mono Ester | Di Ester | % Non-Alkoxy | % Alkoxy | Sample ID |
| 90 | 10 | 90 | 10 | A |
| 90 | 10 | 10 | 90 | C |
| 10 | 90 | 90 | 10 | G |
| 10 | 90 | 10 | 90 | I |
| 90 | 10 | 0 | 100 | M |
| 10 | 90 | 0 | 100 | O |

Emulsions produced with samples J, K and L were not used because they were unstable.
Methodology Oil deposition onto Afro-American hair fibers was determined by the formic acid technique using a Mechanical Tensile Tester Diastron. This method is based on the fact that formic acid diffuses into hair fibers where it breaks the hydrogen and salt bonds present. The breakage of these bonds weaken the hair, allowing it to be more easily stretched. The force necessary to stretch the hair continues to drop as the formic acid penetrates the hair shaft. The time at which the force reaches an equilibrium is expressed as Tf (minutes). Application of the emulsions was carried out by rubbing the cream gently onto the hair for 15 minutes.

In this study the treated hair fiber is immersed in formic acid and repeatedly stretched 1% over its original length. As the formic acid penetrates the hair fiber, the force necessary to stretch it 1% steadily decreases until the time Tf when equilibrium is reached.
Results Table V sets forth the results obtained from the oil deposition study where BW-AP1 is the formula representing 5.75% emulsifier use level and BW-AP3 is the formula representing the 48.6% emulsifier use level based on the oil phase concentration. The suffixes, A, C, G, I, M and O indicate the emulsifier.

TABLE V

| Emulsion ID | Tf (minutes) |
|---|---|
| BW-AP1-A | 1.33 |
| BW-AP1-C | 0.92 |
| BW-AP1-G | 2.15 |
| BW-AP1-I | 0.57 |
| BW-AP1-M | 0.58 |
| BW-AP1-O | 0.57 |
| BW-AP3-A | 1.21 |
| BW-AP3-C | 0.98 |
| BW-AP3-G | 2.50 |
| BW-AP3-I | 0.55 |
| BW-AP3-M | 0.59 |
| BW-AP3-O | 0.57 |
| 3% NaOH Sol. (Control) | 0.58 |

In Table V it can be seen that the control, a fiber relaxed with a 3% NaOH aqueous solution, yields a Tf of 0.58 minutes; this Tf value corresponds to the highest formic acid diffusion rate normally obtained and indicates no oil deposition. We also see that emulsions BW-AP1-I, BW-AP1-M, and BW-AP1-O, as well as BW-AP3-I, BW-AP3-M and BW-AP3-O show no oil deposition while the rest of the emulsions show oil deposition in the following order: BW-AP3-G>BW-AP3-A>BW-AP3-C and BW-AP1-G>BW-AP1-A>BW-AP1-C.

The results show that the emulsions prepared with 100% fatty alkoxy ester phosphate as the emulsifier with mono/di ester ratios ranging from 10/90 and 90/10 (samples M and O) yield no oil deposition. The results also show that emulsions prepared with Sample I, which consists of a mono/diester ratio of 10/90 and a fatty non-alkoxy/fatty alkoxy alcohol ratio of 10/90, also show no oil deposition.

The data for Emulsifier Sample I can be explained by the fact that this emulsifier contains an enormous amount of alkoxylated fatty alcohol ester groups. The monoester to diester ratio is 10:90 and the non-alkoxylated fatty alcohol ester to alkoxylated fatty alcohol ester ratio is also 10:90. Thus, this emulsifier behaves equivalently to emulsifiers containing 100% alkoxylated fatty alcohol esters, i.e., there is good emulsion stability but ineffective oil deposition.
Results Emulsions produced with fatty alkoxy ester phosphates are stable but do not yield any oil deposition. Emulsions produced with fatty non-alkoxy ester phosphates are unstable. Lastly, emulsions prepared with blends of the two types of ester phosphates are stable and yield a desired oil deposition which can offer benefits such as lower hair damage/irritation in products such as hair straighteners or relaxers.

In hair relaxers/straighteners, this oil deposition protects the hair shaft from excessive penetration of the hydroxide ion into the hair shaft which is the cause of the hair damage. The longer time needed for diffusion of formic acid into the hair fibers treated with emulsions based on the invention is the result of the emulsion's oil release onto the hair shaft which acts as a protective barrier. This oil release results from the unique and unexpected properties of the phosphate ester blends of the present invention. Afro-American hair that has been straightened or "relaxed" with products containing the invention shows significantly less cuticle damage compared to products without it. This reduction in cuticle damage is the result of the controlled oil release from the emulsion.

Examples 19–21

Samples of emulsifier compositions in accordance with the present invention were prepared to determine the ratio of non-alkoxy fatty alcohol phosphate esters to alkoxy fatty alcohol phosphate esters effective to produce oil deposition for 10:90 monoester to diester ratios. The emulsifier samples that were prepared are set forth below in Table VI:

TABLE VI

| Ester Distribution (%) | | Fatty Alcohol Ratio | | Emulsifier |
|---|---|---|---|---|
| Mono Ester | Di Ester | (%) Non-Alkoxy | (%) Alkoxy | Sample ID |
| 10 | 90 | 10 | 90 | I |
| 10 | 90 | 15 | 85 | I-1 |
| 10 | 90 | 25 | 75 | I-2 |
| 10 | 90 | 30 | 70 | I-3 |

Synthesis

The alkoxylated alcohol samples were prepared using PEG-10 Cetearyl Alcohol while Cetearyl alcohol was used as the non-alkoxy alcohol. The pure mono and diester phosphates were produced using the teachings of Kurosaki et al., U.S. Pat. Nos. 4,670,575 and 4,587,063, respectively.

Formulation Evaluation

Samples I-1, I-2 and I-3 were used to prepare emulsions at three emulsifier concentrations—5.75 percent, 25 percent and 48.6 percent. The emulsifier levels were again determined based on the oil phase content.

The emulsion formulas BW-AP1, BW-AP2 and BW-AP3 were prepared as set forth in Table VII.

TABLE VII

| INGREDIENT | BW-AP1(%) | BW-AP2(%) | BW-AP3(%) |
|---|---|---|---|
| Petrolatum | 21.00 | 13.00 | 15.00 |
| Mineral Oil | 15.00 | 10.00 | 10.00 |
| Emulsifier | 2.50 | 8.25 | 17.00 |
| CRODACOL 1618 | 7.50 | 10.00 | 10.00 |
| Deionized Water | 44.85 | 49.45 | 38.36 |
| Propylene Glycol | 3.00 | 3.00 | 3.00 |
| Sodium Hydroxide | 2.15 | 2.30 | 2.64 |
| Deionized Water | 4.00 | 4.00 | 4.00 |

Formula BW-AP1 was used in the <10% emulsifier study, BW-AP2 was used in the 25% emulsifier study and BW-AP3 was used in the >40% emulsifier study. A total of 9 emulsions were prepared, the stability observations for which are set forth in Table VIII. CRODACOL 1618 is a mixture of cetyl and stearyl alcohols, also known as cetearyl alcohol

TABLE VIII

| Sample ID | Emulsion BW-AP1 | Emulsion BW-AP2 | Emulsion BW-AP3 |
|---|---|---|---|
| I-1 | Stable | Stable | Stable |
| I-2 | Stable | Stable | Stable |
| I-3 | Stable | Stable | Stable |

The emulsion stability was tested in a 40° C. oven for one month. The nine emulsions were then evaluated for oil deposition properties as in the previous examples.

Oil Deposition—Results

The results obtained from the oil deposition study where BW-AP1 is the formula representing 5.75% emulsifier use level, BW-AP2 is the formula representing the 25% emulsifier use level and BW-AP3 is the formula representing the 48.6% emulsifier use level are shown in Table IX. The emulsifier use level is based on the oil phase concentration. The prefixes I-1, I-2 and I-3 identify the emulsifier used.

TABLE IX

| Emulsion ID | Tf (minutes) | Emulsifier Conc. (%) | Emulsifier Alcohol Ratio | |
|---|---|---|---|---|
| | | | % Non-Alkoxy | % Alkoxy |
| I-1-BW-AP1 | 0.50 | <10 | 15 | 85 |
| I-1-BW-AP2 | 0.59 | 25 | 15 | 85 |
| I-1-BW-AP3 | 0.55 | >40 | 15 | 85 |
| I-2-BW-AP1 | 0.49 | <10 | 25 | 75 |
| I-2-BW-AP2 | 0.52 | 25 | 25 | 75 |
| I-2-BW-AP3 | 0.92 | >40 | 25 | 75 |
| I-3-BW-AP1 | 0.67 | <10 | 30 | 70 |
| I-3-BW-AP2 | 1.45 | 25 | 30 | 70 |
| I-3-BW-AP3 | 1.88 | >40 | 30 | 70 |
| 3% NaOH Sol. | 0.56 | 0 | 0 | 0 |

In the above table it can be seen that the control, a fiber relaxed with a 3% NaOH aqueous solution, yields a Tf of 0.56 minutes; this Tf value corresponds to the highest formic acid diffusion rate normally obtained and indicates no oil deposition.

It can be seen that the three emulsions prepared with sample I-1 gave no oil deposition at the three emulsifier concentrations evaluated. Sample I-2 yielded oil deposition only with emulsion I-2-BW-AP3 which contains the emulsifier at a level <40% of the oil phase.

Sample I-3 produced emulsions which gave oil deposition at all three emulsifier concentrations.

As will now be readily appreciated, the present invention provides emulsifier compositions capable of forming oil-in-water emulsions with unique viscosity, rheology and stability properties. The desirable flakability of the emulsifier compositions of the present invention also satisfy a long-felt and heretofore unmet need for oil-in-water emulsifier compositions.

The foregoing description of the preferred embodiment should be taken as illustrating, rather than as limiting, the present invention as defined by the claims. Numerous variations and combinations of the features described above can be utilized without departing from the present invention.

What is claimed is:

1. An oil-in-water emulsifier composition comprising:
   between about 10 percent and about 70 percent by weight of a blend of mono- and diester phosphates of alkoxylated fatty alcohols containing between about 12 and 22 carbon atoms and alkoxylated with between about 1 and about 50 moles of an alkylene oxide consisting of ethylene oxide, wherein the mono- and di-ester ratio is between about 10:90 and about 90:10; and between about 90 percent and about 30 percent by weight of a blend of mono- and diester phosphates of non-alkoxylated fatty alcohols containing between about 12 and 22 carbon atoms, wherein the mono- and diester ratio is between about 10:90 and about 90:10.

2. The emulsifier composition of claim 1, wherein said alkoxylated and non-alkoxylated fatty alcohols contain from 14 to 20 carbon atoms.

3. The emulsifier composition of claim 1, wherein said alkoxylated fatty alcohol is alkoxylated with between about 2 and about 20 moles of an ethylene oxide.

4. The emulsifier composition of claim 1, wherein said non-alkoxylated fatty alcohol phosphate esters have a ratio of said monoester to said diester of less than about 50:50.

5. The emulsifier composition of claim 1, wherein the level of alkoxylated fatty alcohol phosphate esters is between about 20 percent and about 70 percent by weight.

6. An emulsifying wax composition comprising from about 5 percent to about 90 percent by weight of the emulsifier composition of claim 1 blended with a fatty alcohol containing between 12 and 22 carbon atoms.

7. The emulsifying wax of claim 6, wherein said fatty alcohol contains between 14 and 20 carbon atoms.

8. The emulsifying wax composition of claim 6, comprising from about 5 percent up to about 15 percent by weight of said emulsifier composition.

9. An oil-in-water emulsion comprising from about 2 to about 80 percent by weight of an oil phase, from about 10 to about 98 percent by weight of a water phase, and an amount of the emulsifier composition of claim 1 between about 10 and about 40 percent by weight relative to said oil phase.

10. The oil-in-water emulsion of claim 9, further comprising one or more active ingredients selected from the group consisting of UV-absorbing agents, aqueous moisturizing agents, oily moisturizing agents, film-forming polymers, thickening agents, secondary emulsifiers other than said mono- and diester phosphates of said alkoxylated and non-alkoxylated fatty alcohols, antiseptic agents, skin conditioning agents, hair conditioning agents, deodorant actives, humectants, rheological modifiers, protein reducing agents and protein hydrolyzing agents.

11. The oil-in-water emulsion of claim 10, wherein said secondary emulsifiers comprise one or more detergent surfactants selected from the group consisting of anionic detergents, cationic detergents, nonionic detergents and amphoteric detergents.

12. The oil-in-water composition of claim 10, wherein said one or more active ingredients are present in an amount up to 30 percent w/w of said composition.

13. The oil-in-water emulsion of claim 10, wherein said skin conditioning agents and hair conditioning agents comprise emollients.

14. The oil-in-water emulsion of claim 9, wherein said emulsifier composition is present at a level of about 20 percent by weight of said oil phase.

15. An oil-in-water microemulsion comprising a non-emulsifier portion comprising an oil phase and a water phase, and an emulsifier portion comprising an amount of the emulsifier composition of claim 1 between about 100 and about 300 percent by weight relative to the oil phase.

16. The oil-in-water microemulsion of claim 15, further comprising one or more active ingredients selected from the group consisting of UV-absorbing agents, aqueous moisturizing agents, oily moisturizing agents, film-forming polymers, thickening agents, secondary emulsifiers other than said mono- and diester phosphates of said alkoxylated and non-alkoxylated fatty alcohols, antiseptic agents, skin conditioning agents, hair conditioning agents, deodorant actives, humectants, rheological modifiers, protein reducing agents and protein hydrolyzing agents.

17. The oil-in-water microemulsion of claim 16, wherein said secondary emulsifiers comprise one or more detergent surfactants selected from the group consisting of anionic detergents, cationic detergents, nonionic detergents and amphoteric detergents.

18. The oil-in-water microemulsion of claim 16, wherein said one or more active ingredients are present in an amount up to 30 percent w/w of said composition.

19. The oil-in-water microemulsion of claim 16, wherein said skin conditioning agents and hair conditioning agents comprise emollients.

20. The oil-in-water microemulsion of claim 15, wherein said emulsifier composition is present at a level between about 150 percent and about 275 percent by weight of said oil phase.

21. An oil and water emulsion or microemulsion comprising a non-emulsifier portion comprising an oil phase and a water phase and an emulsifier portion comprising at least about 40% by weight relative to said oil phase of an emulsifier composition comprising between about 10% and about 75% by weight of a blend of mono- and diester phosphates of alkoxylated fatty alcohols containing between about 12 and 22 carbon atoms and alkoxylated with between about 1 and about 50 moles of an alkylene oxide consisting of ethylene oxide, wherein the mono- and diester ratio is between about 10:90 and about 90:10; and between about 25 percent and about 90 percent by weight of a blend of mono- and diester phosphates of non-alkoxylated fatty alcohols containing between about 12 and 22 carbon atoms, wherein the mono- and diester ratio is between about 10:90 and about 90:10.

* * * * *

UNITED STATES PATENT AND TRADEMARK OFFICE
CERTIFICATE OF CORRECTION

PATENT NO. : 6,117,915
DATED : September 12, 2000
INVENTOR(S) : Pereira et al.

It is certified that error appears in the above-identified patent and that said Letters Patent is hereby corrected as shown below:

Column 1,
Line 9, after "reference" insert -- , which was refiled as Divisional application 08/469,999 on June 6, 1995, now U.S. Patent No. 5,633,403. --.

Column 10,
Line 67, after "phase" insert -- content of --.

Column 14,
Line 44, "<40%" should read -- >40% --.

Signed and Sealed this

Twenty-third Day of October, 2001

Attest:

*Nicholas P. Godici*

NICHOLAS P. GODICI
*Attesting Officer*  *Acting Director of the United States Patent and Trademark Office*